United States Patent [19]

Cartwright

[11] Patent Number: 4,780,128
[45] Date of Patent: * Oct. 25, 1988

[54] HERBICIDES

[75] Inventor: David Cartwright, Woodley, England

[73] Assignee: Imperial Chemical Industries PLC, London, England

[*] Notice: The portion of the term of this patent subsequent to Aug. 25, 1998 has been disclaimed.

[21] Appl. No.: 901,998

[22] Filed: Aug. 28, 1986

Related U.S. Application Data

[63] Continuation of Ser. No. 411,006, Aug. 24, 1982, abandoned, which is a continuation of Ser. No. 168,785, Jul. 14, 1980, abandoned.

[30] Foreign Application Priority Data

Jul. 18, 1979 [GB] United Kingdom ............... 7925032
Nov. 8, 1979 [GB] United Kingdom ............... 7938804

[51] Int. Cl.$^4$ .................. A01N 37/18; C07C 143/78
[52] U.S. Cl. ........................................ 71/103; 564/99; 564/95
[58] Field of Search ................ 71/103; 564/99, 95

[56] References Cited

U.S. PATENT DOCUMENTS

| | | | |
|---|---|---|---|
| 3,878,236 | 4/1975 | Gates et al. | 71/103 |
| 4,058,392 | 11/1977 | Thomas et al. | 71/106 |
| 4,262,152 | 4/1981 | Johnson | 560/21 |
| 4,285,723 | 8/1981 | Cartwright et al. | 71/103 |

*Primary Examiner*—Catherine L. Mills
*Attorney, Agent, or Firm*—Cushman, Darby & Cushman

[57] ABSTRACT

Diphenyl ethers of formula:

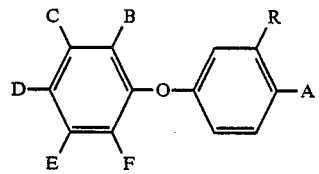

wherein A is hydrogen or one of a specified range of substituents e.g. halogen, hydroxy, haloalkyl, B, C, E and F are hydrogen or specified substituents; D is $CF_3$, halogen, or another specified substituent; and R is a group $—CONR^4SO_2R^3$ wherein $R^4$ is hydrogen or $C_1$ to $C_4$ alkyl and $R^3$ is an optionally substituted alkyl, alkenyl, alkynyl, or aryl radical; useful as selective herbicides.

5 Claims, No Drawings

HERBICIDES

This is a continuation of application Ser. No. 411,006, filed Aug. 24, 1982, abandoned, which is a continuation of application Ser. No. 168,785, filed July 14, 1980, abandoned.

This invention relates to chemical compounds useful as herbicides, and to herbicidal compositions and processes utilising them.

In our European patent application No. 79300098.5 there are claimed herbicidal diphenyl ether compounds of the formula (I),

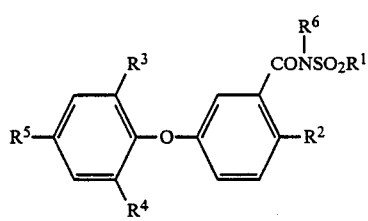

and salts thereof, wherein $R^1$ is an alkyl group of 1 to 6 carbon atoms optionally substituted by one or more fluorine atoms, or by a phenyl group optionally substituted by one or more halogen atoms; $R^2$ is a hydrogen atom, a fluorine, chlorine, bromine, or iodine atom, or a nitro group; $R^3$ is a hydrogen atom, a fluorine, chlorine, bromine, or iodine atom, an alkyl group of 1 to 6 carbon atoms, a trifluoromethyl group, or a cyano group; $R^4$ is a hydrogen atom, a fluorine, chlorine, bromine, or iodine atom, or a trifluoromethyl group; $R^5$ is a fluorine, chlorine, bromine, or iodine atom or a trifluoromethyl group; and $R^6$ is a hydrogen atom or an alkyl group of 1 to 4 carbon atoms.

In the present application we make no claim to any compound claimed in European patent application No. 79300098.5. Subject to this disclaimer, the present invention provides diphenyl ether compounds of formula (II)

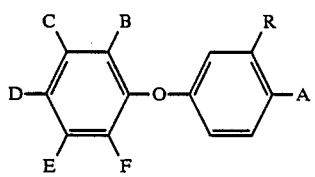

wherein A is hydrogen; halogen; $NO_2$; $N=N-CF_3$; $PO_3H_2$ and $C_1$ to $C_4$ alkyl esters thereof; a carboxy group or a functional derivative thereof; $NH_2$; NHOH; $-N_2^+$; mono or dialkylamino; $NHCOR^1$ wherein $R^1$ is alkyl or alkoxy or mono- or dialkylamino; alkyl; mono- or dialkylamino; trialkylammonio; $NHSO_2R^2$ where $R^2$ is an alkyl or phenyl radical; $-NHCONHSO_2R^2$; alkylthio; alkylsulplhinyl; alkylsulphonyl; dialkylsulphonio; cyanosulphonyl; hydroxy; alkanoyloxy; alkoxy; alkoxy substituted by alkoxy carbonyl; —SH; —N=O; —SCN; $N_3$; $CF_3$;

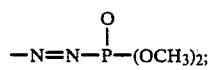

or acyl;

B is hydrogen; fluorine; chlorine; bromine; iodine; alkyl; alkoxy; alkylsulphinyl; alkylsulphonyl; $CF_3$; $NO_2$; CN; $NH_2$; $NHCOR^1$ where $R^1$ is defined as above; or $CONH_2$;

C is hydrogen, halogen, alkyl, or dialkylamino;

D is $CF_3$; alkylthio; alkylsulphinyl; alkylsulphonyl; halogeno; alkyl; sulphamoyl; formyl; alkylcarbonyl; CN; or $N(CH_3)_2$;

E is hydrogen, halogeno, alkyl; alkoxy; alkylsulphinyl; alkylsulphonyl; CN; $CF_3$; $NH_2$; $NHCOR^1$; or $CONH_2$;

F is defined as for B above;

and R is a group $—CONR^4SO_2R^3$ where $R^4$ is hydrogen or an alkyl group of 1 to 4 carbon atoms and $R^3$ is a phenyl, pyridyl or thienyl radical optionally substituted by one or more halogen atoms, alkyl groups, or nitro groups, or an alkenyl or alkynyl radical of 2 to 4 carbon atoms or an alkyl radical of 1 to 4 carbon atoms optionally substituted by one or more atoms of chlorine, bromine, or iodine, or by one or more of the following substituents; carboxyl; alkoxycarbonyl of two to five carbon atoms; alkylcarbonyl, of two to five carbon atoms; mono- or di-alkyl carbamoyl in which the alkyl groups have from one to four carbon atoms; alkoxy of one to four carbon atoms; alkylthio, alkylsulphinyl, or alkylsulphonyl all of one to four carbon atoms; alkylcarbonyloxy of two to five carbon atoms; alkylcarbonylamino of two to five carbon atoms; or cyano.

In the foregoing definition, the expression "carboxyl group or a functional derivative thereof" is intended to include esters, amides, and salts of the carboxylic function, including for example substituted amides of formula $CONHSO_2R^3$ as defined above and oximes of the formula

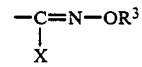

wherein X is chlorine, cyano, nitro, or an acyl group

wherein $R^5$ is an alkyl group of 1 to 4 carbon atoms.

Where reference is made above to alkyl radicals or radicals containing one or more alkyl groups, for example mono- and di-alkylamino, or alkoxy, the alkyl radical may be for example a lower alkyl radical having for example 1 to 6 carbon atoms.

One sub-group of compounds according to the invention comprises compounds of formula (II) wherein A is hydrogen, fluorine, chlorine, bromine, iodine or a nitro group;

B is a nitro group;

C is hydrogen;

D is fluorine, chlorine, bromine, iodine, or a $CF_3$ group;

E is hydrogen;

F is hydrogen, fluorine, chlorine, bromine, iodine, or $CF_3$ and R is a $—CONHSO_2R^3$ group wherein $R^3$ is an alkenyl or alkynyl² group of 2 to 4 carbon atoms or an optionally substituted alkyl group of 1 to 4 carbon atoms.

Another sub group comprises compounds in which the group

Examples of compounds of the invention are listed in Table 1 below:

TABLE I $$\text{(II)}$$

Structure: a diphenyl ether with substituents C, B on one ring (and D, E, F), linked via O to a second ring bearing A and CONHSO$_2$R$^3$.

| COMPOUND NO | A | B | C | D | E | F | R$^3$ | MELTING POINT °C. |
|---|---|---|---|---|---|---|---|---|
| 1 | NO$_2$ | Cl | H | CF$_3$ | H | H | C$_6$H$_5$ | 123–125 |
| 2 | NO$_2$ | Cl | H | CF$_3$ | H | H | 5-indanyl | 110–112 |
| 3 | NO$_2$ | Cl | H | CF$_3$ | H | H | .C$_6$H$_3$.2-NO$_2$—4Cl | 154–156 |
| 4 | NO$_2$ | Cl | H | CF$_3$ | H | H | .C$_6$H$_3$.2-Cl,5-NO$_2$ | 180–183 |
| 5 | NO$_2$ | Cl | H | CF$_3$ | H | H | .C$_6$H$_4$.p.CH$_3$ | 105–108 |
| 6 | NO$_2$ | Cl | H | CF$_3$ | H | H | —(CH$_2$)$_3$Cl | 116–119 |
| 7 | NO$_2$ | Cl | H | CF$_3$ | H | H | —CH$_2$CO$_2$CH$_3$ | 158–160 |
| 8 | NO$_2$ | Cl | H | CF$_3$ | H | H | —CH$_2$Cl | 145–148 |
| 9 | NO$_2$ | Cl | H | CF$_3$ | H | H | .C$_6$H$_4$.pI | 167 |
| 10 | NO$_2$ | Cl | H | Cl | H | H | .(CH$_2$)$_3$Cl | 176–178 |
| 11 | H | Cl | H | F$_3$ | H | H | .(CH$_2$)$_3$Cl | 118–120 |
| 12 | NHCOCH$_3$ | Cl | H | CF$_3$ | H | H | CH$_3$ | 201 |
| 13 | NHCOCF$_3$ | Cl | H | CF$_3$ | H | H | CH$_3$ | 207 |
| 14 | NHSO$_2$CH$_3$ | Cl | H | CF$_3$ | H | H | CH$_3$ | 169 |
| 15 | NHCO$_2$C$_2$H$_5$ | Cl | H | CF$_3$ | H | H | CH$_3$ | 204 |
| 16 | NHCON(CH$_3$)$_2$ | Cl | H | CF$_3$ | H | H | .CH$_3$ | 156 |
| 17 | N=N—CF$_3$ | Cl | H | CF$_3$ | H | H | CH$_3$ | 151 |
| 18 | NHOH | Cl | H | CF$_3$ | H | H | CH$_3$ | 143 |
| 19 | N$_2$ | Cl | H | CF$_3$ | H | H | CH$_3$ | 160 |
| 20 | CH$_3$ | Cl | H | CF$_3$ | H | H | CH$_3$ | 142 |
| 21 | NO$_2$ | NO$_2$ | H | CF$_3$ | H | H | CH$_3$ | 184–188 |
| 22 | NO$_2$ | Cl | H | Cl | Cl | H | CH$_3$ | 170–171 |
| 23 | NO$_2$ | NO$_2$ | H | CF$_3$ | H | Cl | CH$_3$ | 206 |
| 24 | NH$_2$ | Cl | H | CF$_3$ | H | H | CH$_3$ | 184–185 |
| 25 | NO$_2$ | NO$_2$ | H | CH$_3$ | H | H | CH$_3$ | 123 dec. |
| 26 | —SCN | Cl | H | CF$_3$ | H | H | CH$_3$ | 135 dec. |
| 27 | —N$_3$ | Cl | H | CF$_3$ | H | H | CH$_3$ | 119 dec. |
| 28 | NO$_2$ | SOCH$_3$ | H | CF$_3$ | H | H | CH$_3$ | 158–160 |
| 29 | —N=N—P(OCH$_3$)$_2$ | Cl | H | CF$_3$ | H | H | CH$_3$ | 159 dec. |
| 30 | NO$_2$ | F | F | CF$_3$ | F | F | CH$_3$ | 177–177.5 |
| 31 | H | Cl | H | H | CF$_3$ | H | CH$_3$ | 132–133 |
| 32 | NO$_2$ | Cl | H | H | CF$_3$ | H | CH$_3$ | 204–205 |
| 33 | H | Cl | H | NO$_2$ | H | H | CH$_3$ | 212–214 |
| 34 | NO$_2$ | H | Cl | H | Cl | H | CH$_3$ | 156 |
| 35 | H | NO$_2$ | H | CF$_3$ | H | H | CH$_3$ | 155–157 |
| 36 | NO$_2$ | NO$_2$ | H | Cl | H | H | CH$_3$ | 117–121 |
| 37 | CF$_3$ | Cl | H | CF$_3$ | H | H | CH$_3$ | 188 |
| 38 | NO$_2$ | H | CH$_3$ | Cl | H | H | CH$_3$ | 171–173 |

Compound 19 exists largely as the cyclic compound

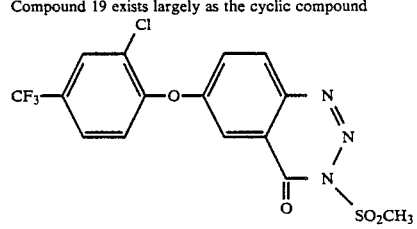

A is methyl or trifluoromethyl;
B is fluorine or chlorine;
C is hydrogen;
D is fluorine, chlorine, bromine, iodine, or CF$_3$;
E is hydrogen;
F is hydrogen, fluorine, chlorine, bromine, iodine, or CF$_3$;
and R is a —CONHSO$_2$R$^3$ group wherein R$^3$ is an alkynyl or alkenyl group of 2 to 4 carbon atoms or an optionally substituted alkyl group of 1 to 4 carbon atoms.

Further examples of compounds according to the invention are listed in Tbale II below:

TABLE II

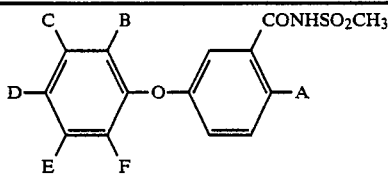

| COMPOUND NO | A | B | C | D | E | F |
|---|---|---|---|---|---|---|
| 43 | NO$_2$ | H | H | CO$_2$CH$_3$ | H | H |
| 44 | NO$_2$ | CH$_3$ | H | CH$_3$S | H | CH$_3$ |
| 45 | NO$_2$ | CH$_3$ | H | CH$_3$SO | H | CH$_3$ |
| 46 | NO$_2$ | CH$_3$ | H | CH$_3$SO$_2$ | H | CH$_3$ |
| 47 | NO$_2$ | H | H | CH$_3$SO$_2$ | H | H |
| 48 | NO$_2$ | Cl | H | CH$_3$SO$_2$ | H | H |
| 49 | NO$_2$ | NO$_2$ | H | Cl | H | H |
| 50 | NO$_2$ | H | H | CON(CH$_3$)$_2$ | H | H |
| 51 | NO$_2$ | CH$_3$O | H | Cl | H | H |
| 52 | NO$_2$ | CH$_3$O | H | H | H | H |
| 53 | NO$_2$ | H | H | SO$_2$NH$_2$ | H | H |
| 54 | NO$_2$ | NO$_2$ | H | CH$_3$ | H | H |
| 55 | NO$_2$ | H | H | t C$_4$H$_9$ | H | H |
| 56 | NO$_2$ | H | H | CH$_3$CO | H | H |
| 57 | NO$_2$ | Cl | H | t C$_4$H$_9$ | H | H |
| 58 | NO$_2$ | H | H | CN | H | H |
| 59 | NO$_2$ | Cl | H | CF$_3$ | H | NH$_2$ |
| 60 | NO$_2$ | F | H | CF$_3$ | H | NH$_2$ |
| 61 | NO$_2$ | H | H | SCH$_3$ | H | H |
| 62 | NO$_2$ | H | H | SOCH$_3$ | H | H |
| 63 | NO$_2$ | NO$_2$ | H | C(CH$_3$)$_3$ | H | H |
| 64 | NO$_2$ | Cl | H | OCH$_3$ | H | H |
| 65 | SC$_2$H$_5$ | Cl | H | CF$_3$ | H | H |
| 66 | SH | Cl | H | CF$_3$ | H | H |
| 67 | SCH$_3$ | Cl | H | CF$_3$ | H | H |
| 68 | SOCH$_3$ | Cl | H | CF$_3$ | H | H |
| 69 | SO$_2$CH$_3$ | Cl | H | CF$_3$ | H | H |
| 70 | NHCH$_3$ | Cl | H | CF$_3$ | H | H |
| 71 | OH | Cl | H | CF$_3$ | H | H |
| 72 | OCH$_3$ | Cl | H | CF$_3$ | H | H |
| 73 | OCH(CH$_3$)CO$_2$CH$_3$ | Cl | H | CF$_3$ | H | H |
| 74 | OCOCH$_3$ | Cl | H | CF$_3$ | H | H |
| 75 | N(CH$_3$)$_2$ | Cl | H | CF$_3$ | H | H |

Further examples of compounds falling within the scope of the invention are listed in Table IIA.

TABLE IIA

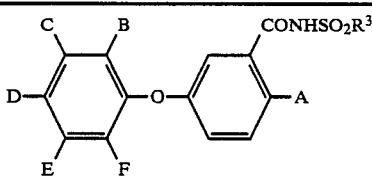

| COMPOUND NO | A | B | C | D | E | F | R$^3$ |
|---|---|---|---|---|---|---|---|
| 76 | NO$_2$ | CF$_3$ | H | Cl | H | H | .CH(CH$_3$)CO$_2$CH$_3$ |
| 77 | NO$_2$ | Cl | H | Cl | H | H | .CH$_2$CH$_2$Cl |
| 78 | NO$_2$ | Cl | H | CF$_3$ | H | H | .CHCl$_2$ |
| 79 | Cl | Cl | H | CF$_3$ | H | H | .CH$_2$CON(CH$_3$)$_2$ |
| 80 | NO$_2$ | Cl | H | CF$_3$ | H | H | 3-pyridyl |
| 81 | NO$_2$ | CF$_3$ | H | Cl | H | H | .CH$_2$CH$_2$OCOCH$_3$ |
| 82 | NO$_2$ | Cl | H | CF$_3$ | H | H | .CH$_2$CH$_2$OCH$_3$ |
| 83 | Cl | CF$_3$ | H | Cl | H | H | .CH$_2$CH$_2$NHCOCH$_3$ |
| 84 | NO$_2$ | Cl | H | CF$_3$ | H | H | .CH(CH$_3$)CN |
| 85 | NO$_2$ | Cl | H | CF$_3$ | H | H | .CH$_2$COCH$_3$ |
| 86 | NO$_2$ | Cl | H | CF$_3$ | H | H | .CH$_2$CH$_2$SCH$_3$ |
| 87 | NO$_2$ | Cl | H | CF$_3$ | H | H | .CH$_2$CH$_2$SOCH$_3$ |
| 88 | NO$_2$ | Cl | H | CF$_3$ | H | H | .CH$_2$CH$_2$SO$_2$CH$_3$ |
| 89 | NO$_2$ | Cl | H | CF$_3$ | H | H | .C$_6$H$_4$.oCl |

TABLE IIA-continued

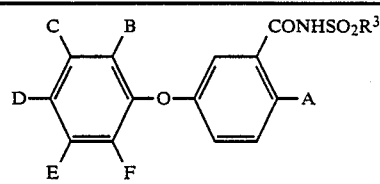

| COMPOUND NO | A | B | C | D | E | F | R$^3$ |
|---|---|---|---|---|---|---|---|
| 90 | NO$_2$ | Cl | H | CF$_3$ | H | H | .C$_6$H$_4$.OCH$_3$p |
| 91 | NO$_2$ | Cl | H | CF$_3$ | H | H | 2-pyridyl |
| 92 | NO$_2$ | Cl | H | CF$_3$ | H | H | 2-thienyl |
| 93 | NO$_2$ | Cl | H | CF$_3$ | H | F | .CH$_2$CH$_2$OCH$_3$ |
| 94 | NO$_2$ | Cl | H | CF$_3$ | H | H | .CH=CH$_2$ |
| 95 | NO$_2$ | Cl | H | CF$_3$ | H | F | .CH$_2$CCH |
| 96 | Cl | Cl | H | CF$_3$ | H | H | .CH$_2$CH=CH$_2$ |
| *97 | NO$_2$ | Cl | H | CF$_3$ | H | F | .CH$_2$CH$_2$CH$_2$Cl |

*Melting point 150-151°

As explained below, the compounds of the invention may in general be made from the corresponding compounds of formula II above wherein R is a carboxyl group.

Table III below gives melting points for compounds which may be used as intermediates for the synthesis of the compounds listed in Table II.

TABLE III

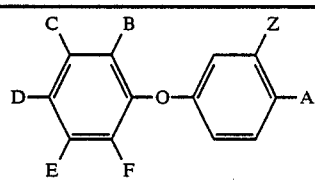

| INTERMEDIATE FOR COMPOUND NO (see Table II) | Z | MELTING POINT °C. |
|---|---|---|
| 43 | CO$_2$CH$_3$ | 86-90 |
| 44 | CO$_2$CH$_3$ | 68-69 |
| 45 | CO$_2$CH$_3$ | 115-116 |
| 46 | CO$_2$CH$_3$ | 172-173 |
| 47 | CO$_2$CH$_3$ | 120-121 |
| 48 | CO$_2$H | 187-189 |
| 49 | CO$_2$H | 207-209 |
| 50 | CO$_2$N(CH$_3$)$_2$ | 141-145 |
| 51 | CO$_2$CH$_3$ | 64-65 |
| 52 | CO$_2$CH$_3$ | 66-68 |
| 53 | CO$_2$CH$_3$ | 149-153 |
| 54 | CO$_2$CH$_3$ | 99-100 |
| 55 | CO$_2$CH$_3$ | 89-90 |
| 56 | CO$_2$CH$_3$ | 105-107 |
| 57 | CO$_2$CH$_3$ | 94-96 |
| 58 | CO$_2$CH$_3$ | 94-96 |
| 59 | CO$_2$CH$_3$ | 168-170 |
| 60 | CO$_2$CH$_3$ | 138-139 |
| 61 | CO$_2$CH$_3$ | 95-97 |
| 62 | CO$_2$CH$_3$ | 108-109 |
| 63 | CO$_2$CH$_3$ | 91-93 |
| 64 | CO$_2$CH$_3$ | 84-86 |
| 65 | CO$_2$CH$_3$ | 153-155 |
| 66 | CO$_2$CH$_3$ | Oil |
| 67 | CO$_2$CH$_3$ | Oil |
| 68 | CO$_2$CH$_3$ | 130 |
| 69 | CO$_2$CH$_3$ | 125 |
| 70 | CO$_2$CH$_3$ | 94 |
| 71 | CO$_2$CH$_3$ | 137 |
| 72 | CO$_2$CH$_3$ | 73 |
| 73 | CO$_2$CH$_3$ | 73 |
| 74 | CO$_2$CH$_3$ | Oil, b.p. 180°/1 Torr. |
| 75 | CO$_2$CH$_3$ | 76° |

Most of the compounds listed in Table III are esters, with one amide. The esters and the amide may be hydrolysed to the corresponding carboxylic acids (Formula II, R=CO$_2$H) by conventional acid or base hydrolysis and the acids converted to the sulphonamide derivatives of the invention as described below. Certain of the carboxylic acids are new compounds, and form a further part of the present invention, together with their salts, esters (e.g. alkyl esters), and amides.

These compounds are themselves herbicidal and may be useful as herbicides, as well as being useful as intermediates for the compounds of the invention. In particular, the compound 5-(2-chloro-4-trifluoromethylphenoxy)-2-trifluoromethylbenzoic acid, described in Example 18 as an intermediate for compound 37 of the invention, is believed to be a new compound and together with its salts, esters, and amides, forms a further part of the invention.

The compounds of the invention may be prepared by a variety of methods. In one method outlined in Scheme A below, a suitably substituted diphenyl ether derivative (III) bearing a carboxyl group is converted to the corresponding carbonyl chloride by reaction with a chlorinating agent according to standard methods. The carbonyl chloride (IV) so obtained is then reacted with an alkanesulphonamide R$^3$SO$_2$NH$_2$ in the presence of an acid acceptor, to give the compound of the invention. Examples of acid acceptors include tertiary amines, for example pyridine and triethylamine. Other acid acceptors include alkali metal carbonates, e.g. anhydrous potassium carbonate. Alkali metal fluorides, especially caesium fluoride, may also be used.

Scheme A

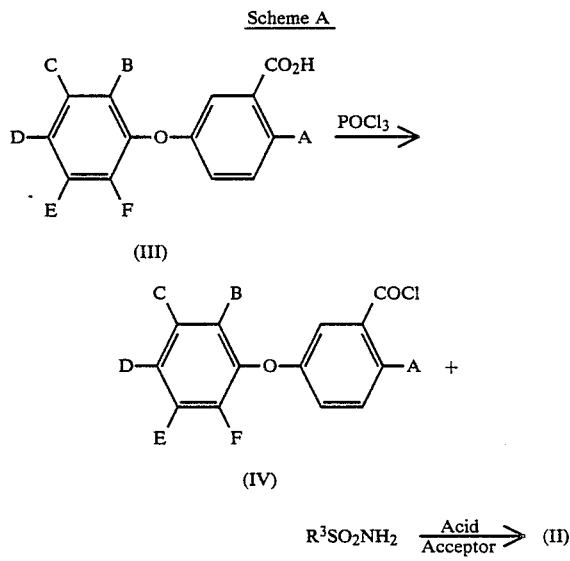

In Scheme A, the starting material (III) may be one that contains all the required substituents for the final product (II). Alternatively, one or more of the substituents may be introduced after the —CONHSO$_2$R$^3$ substituent has been built on to the molecule. Thus, if the substituent A is to be a nitro group in the final product, the reaction Scheme A may start with a compound in which the substituent A is hydrogen and the nitro group may be introduced by a conventional nitration procedure at the last step, following the second reaction shown in Scheme A. In another approach, a compound II may be prepared and one or more of the substituents may be modified by conventional chemical procedures.

Thus compounds (II) wherein A is an amino group may be prepared by reduction of compounds (II) wherein A is a nitro group.

The carboxyl-substituted diphenyl ether derivatives (III) may be obtained by various synthetic methods. In one method, an appropriately substituted phenol may be reacted in salt form with an ester (e.g. the methyl ester) of 3-carboxy-4-nitrofluorobenzene as described in Example 8 for compound 38 of Table 1. The ester so obtained may then be hydrolysed (e.g. by treatment with a mixture of acetic acid and aqueous hydrobromic acid) to the corresponding carboxylic acid (III).

In another method, the same reaction sequence may be carried through, but using an ester of 3-carboxy-4-nitrochlorobenzene instead of an ester of 3-carboxy-4-nitrofluorobenzene, as described in Example 6.

In another method, 3-hydroxybenzoic acid or a 2-substituted-5-hydroxybenzoic acid may be reacted in the form of its di-salt with an appropriately substituted fluoro- or chlorobenzene, as described in Examples 17 and 5.

By way of further illustration of the methods of preparing the compounds of the invention, the following description gives details of the preparation of a number of compounds of formula (III). Each preparation is prefixed by the word "Intermediate" and the number of the compound in Table I or Table II for which the compound is an intermediate. Thus "Intermediate 65" means that the compound prepared is the carboxylic acid of formula III (or its ester) which can be used in the preparation of compound 65 of Table II.

Intermediate 35

3-Hydroxybenzoic acid (13.8 g) in dry dimethylformamide (100 ml) was heated and stirred for 7 hours at 100° with anhydrous potassium carbonate (26 g) and 4-chloro-3-nitrobenzotrifluoride (22.5 g). The mixture was then evaporated to a small volume under reduced pressure and diluted with water. With warming, a dark solution was obtained. Acidification gave a white precipitate; this was washed with water and recrystallised from a mixture of methanol and water to give 3(2-nitro-4-trifluoromethylphenoxy) benzoic acid (24 g).

Intermediate 59

(a) Preparation of
2-amino-6-chloro-4-trifluoromethylphenol

Solid sodium dithionite (10 g) was added in portions to a stirred solution of 2-chloro-6-nitro-4-trifluoromethylphenol (4.5 g) in a mixture of ethanol (20 ml) and water (30 ml). The solution was stirred for 2 hours, left overnight, filtered, and evaporated. The residue was mixed with toluene and the toluene removed under reduced pressure. The residue was extracted with boiling chloroform (3×100 ml) and the chloroform extracts evaporated to give a yellow oil identified as the required substituted phenol.

(b) Preparationl of methyl
5-(2-amino-6-chloro-4-trifluoromethylphenoxy)-2-nitrobenzoate The phenol prepared in (b) (1.5 g) was stirred with methyl 5-fluoro-2-nitrobenzoate (1.4 g) and anhydrous Zpotassium carbonate (2.0 g) in dry dimethylsulphoxide (20 ml) for 3 hours at 150°. The mixture was then cooled, diluted with water, neutralised with dilute hydrochloric acid. The solid which separated was dissolved in dilute sodium hydroxide solution. The solution was extracted twice with ether and then brought to pH 5-6 (HCl). The solid which separated was identified as the required Intermediate 59.

Intermediate 65

2-Iodo-5-(2-chloro-4-trifluoromethylphenoxy) benzoic acid (0.1 mole) in dimethylformamide (500 ml) was cooled to 0°. Cuprous oxide (0.11 mole) was added, followed by ethyl mercaptan (0.1 mole). The mixture was stirred while sodium hydride (0.25 mole) was added in portions. After 15 minutes the temperature was raised to 80° for 6 hours. The mixture was cooled and poured into hydrochloric acid (2 molar). The mixture was twice extracted with ether. The ether extract was washed with water, dried ($Na_2SO_4$) and evaporated. The residue was recrystallised from ether to give 2-ethylthio-5-(2-chloro-4-trifluoromethylphenoxy)benzoic acid, with a melting point of 153°–155°.

Intermediate 66

Methyl 2-diazo-5(2-chloro-4-trifluoromethylphenoxy) benzoate tetrafluoborate (15.0 g, prepared as described in Example 18) was added portionwise at 30° to a stirred solution of tetramethylthiourea (4.0 g) in acetonitrile (50 ml). The mixture was stirred for a further forty-five minutes at 50°, an excess of sodium iodide added to decompose any remaining diazonium salt and the solvent removed in vacuo. The residue was triturated many times, first with water, then ether. The oil was dissolved in dichloromethane, dried and evaporated to give a solid salt.

This salt (3.65 g) was stirred with N sodium hydroxide solution until homogeneous (approximately thirty minutes). The solution was extracted with ether, acidified with 2N hydrochloric acid and again extracted with ether. The latter extracts were washed with water and brine, dried and evaporated to give Intermediate 66 (1.11 g).

Intermediate 67

A solution of methyl 2-mercapto-5(2-chloro-4-trifluoromethylphenoxy)benzoate (1.76 g, prepared as described in Intermediate 66) in N,N-dimethylacetamide (10 ml) was treated with sodium hydride (0.24 g, 50%, prewashed with petroleum b.p. 40°–60°). The mixture was stirred for ten minutes, treated with methyl iodide (0.5 ml, excess) and stirred for a further fifteen minutes. It was then diluted with water and extracted with ether. The extracts were washed with water and brine, dried and evaporated to give Intermediate 67.

Intermediate 68

A solution of methyl 2-methylthio-5(2-chloro-4-trifluoromethylphenoxy) benzoate (1.55 g) in methanol (50 ml) was treated with sodium metaperiodate (0.9 g) in water (10 ml). The mixture was heated at 80° for one hour, cooled, diluted with water and extracted with ethyl acetate. The extracts were washed with water, dried, evaporated and the residue chromatographed on silica in ether to give Intermediate 68 (0.65 g, mp 130°).

Intermediate 69

A solution of methyl 2-methylthio-5(2-chloro-4-trifluoromethylphenoxy)benzoate (1.55 g) and m-chloroperbenzoic acid (3.42 g, excess) in dichloromethane (50 ml) was refluxed for four hours, cooled, diluted with dichloromethane and washed with sodium bicarbonate solution, water and brine. The extracts were dried, evaporated and triturated with petroleum (b.p. 40°–60°) to give Intermediate 69 (1.1 g, m.p. 125°).

Intermediates 70 and 75

A mixture of methyl 2-amino-5(2-chloro-4-trifluoromethylphenoxy)benzoate (3.0 g) and dimethylmethylphosphonate (10 ml) was heated at 120° for four hours. It was then cooled, diluted with water, basified with 2N sodium hydroxide solution and extracted with ether. The extracts were washed with water and brine, dried and evaporated in vacuo to give a brown oil. Trituration with methanol gave Intermediate 70 (0.49 g, m.p. 94°).

A similar experiment was carried out with the exception that the reaction period was extended to twenty hours at 170°. The mixture was cooled, diluted with water and sodium hydroxide solution and extracted with ethyl acetate. The extracts were washed with water and brine, dried and evaporated in vacuo. The residue was triturated with methanol to give Intermediate 75 (1.83 g, m.p. 76°). Intermediate 75 was also prepared by reductive alkylation. Thus treatment of the amine (0.43 g) with formaldehyde (40%, 1.5 ml), sodium cyanoborohydride (0.25 g) and acetic acid (0.13 ml) gave rise to 0.30 g of crude material contaminated with approximately 10% of Intermediate 70.

Intermediate 71

2,5-Dihydroxybenzoic acid (1.68 g) was added portionwise to a stirred suspension of sodium hydride (1.68 g, 50%, prewashed with petroleum b.p. 40°–60°) in N,N-dimethylacetamide (50 ml). The mixture was stirred for a further thirty minutes, then treated with 3-chloro-4-fluorobenzotrifluoride* (2.24 g). It was then heated at 120° for one hour, cooled, diluted with water, acidified with 2N hydrochloric acid and extracted with ethyl acetate. The extracts were washed with water and brine, dried and evaporated in vacuo. The residue was triturated with petroleum (b.p. 40°–60°) and the resulting solid recrystallized from petroleum (b.p. 80°–100°) to give Intermediate 71 (1.55 g, m.p. 137°).

*3,4-Dichlorobenzotrifluoride can also be employed but the period of reaction is extended to thirteen hours at 150° and purification more complex.

A mixture of this material (1.35 g), methanol (25 ml) and borontrifluoride etherate (2 ml) was refluxed for twelve hours, treated with a further portion of the catalyst (1 ml) and refluxing continued for six hours more. Water was then added and the mixture extracted with ether. The extracts were washed with water and brine, dried, evaporated and the residue recrystallized from methanol to give the methyl ester of Intermediate 71 (1.04 g, m.p. 75°).

Intermediates 72, 73 and 74

Methyl 2-hydroxy-5(2-chloro-4-trifluoromethylphenoxy)benzoate (0.35 g, prepared as above was added portionwise to a stirred suspension of sodium hydride (0.05 g, 50%, prewashed with petroleum b.p. 40°–60°) in dimethylacetamide (5 ml). The mixture was stirred for a further thirty minutes, treated with methyl iodide (0.1 ml, excess), and heated at 60° for one hour. It was then diluted with water and extracted with ether. The extracts were washed with water and brine, dried and evaporated and the residue recrystall-ized from petroleum (b.p. 40°–60°) to give Intermediate 72 (250 mg, m.p. 73°).

A similar reaction utilising methyl alpha bromopropionate in place of methyl iodide and extending the reaction period to two hours at 90° gave Intermediate 73 (m.p. 73°).

A similar reaction utilising acetyl chloride in place of methyl iodide proceeded instantaneously to give Intermediate 74 [b.p. 180°(bath)/1 mm].

The compounds of the invention are useful both as pre- and post-emergence herbicides. Pre-emergence herbicides are usually used to treat the soil in which a crop is to be planted, by application before or during seeding, or after seeding and before the crop emerges. Post-emergence herbicides are applied after the crop plants have emerged from the soil. Compounds of the invention may be used as selective herbicides in a variety of crops, including for example cotton, soya bean, peanuts, peas, wheat, sugar beet, barley and rice. Compounds of the invention may also be used as total herbicides. The compounds of the invention may be applied by any of the conventional techniques for applying herbicides. When applied as pre-emergence herbicides they may for example be sprayed on the surface of the soil before or during seeding, or after seeding and before emergence of the crop. In some situations for example in pre-emergence application to soya bean crops it may be advantageous to incorporate the compound of the invention into the soil before planting the crop. This may be done by applying the compound to the surface of the soil and then discing or harrowing the soil to mix the compound with the soil. Alternatively use may be made of the applicators which have been developed for placing herbicides in a band beneath the surface of the soil.

In another aspect, therefore, the invention provides a process of killing or severely injuring unwanted plants, which comprises applying to the plants or to the locus thereof, a compound of the formula (II) or a salt thereof as hereinbefore defined.

As will be understood by those skilled in the art, the amount of the compound (II) applied will depend upon a variety of factors, for example the particular compound chosen for use and the identity of the unwanted plants. By way of general guidance, however, an amount of from 0.1 to 5.0 kilograms per hectare is usually suitable, while from 0.25 to 1.0 kilograms per hectare is preferred.

The compounds used in the process of the invention are preferably applied in the form of a composition, in which the active ingredient is mixed with a carrier comprising a solid or liquid diluent. In another aspect, therefore, the invention provides a herbicidal composition, comprising as an active ingredient a compound of the formula (II) as hereinbefore defined, in admixture with a solid or liquid diluent. Preferably the composition also comprises a surface-active agent.

The solid compositions of the invention may be for example, in the form of dusting powders, or may take the form of granules. Suitable solid diluents include, for example, kaolin, bentonite, kieselguhr, dolomite, calcium carbonate, talc, powdered magnesia, and Fuller's earth. Solid compositions also include soluble powders and granules which may comprise a salt of a compound of the invention in admixture with a water-soluble carrier, or a mixture of a compound of the invention with an alkali for example sodium or potassium carbonate; when mixed with water the composition gives a solution of a salt of the compound of the invention.

Solid compositions may also be in the form of dispersible powders or grains comprising in addition to the active ingredient, a wetting agent to facilitate the dispersion of the powder or grains in liquids. Such powders or grains may include fillers, suspending agents and the like.

Liquid compositions include aqueous solutions, dispersions and emulsions containing the active ingredient preferably in the presence of one or more surface active agents. Water or organic liquids may be used to prepare solutions, dispersions, or emulsions of the active ingredient. The liquid compositions of the invention may also contain one or more corrosion inhibitors for example lauryl isoquinolinium bromide.

Surface active agents may be of the cationic, anionic or non-ionic type. Suitable agents of the cationic type include for example quaternary ammonium compounds, for example cetyltrimethyl ammonium bromide. Suitable agents of the anionic type include for example soaps, salts of aliphatic mono-esters of sulphuric acid, for example sodium lauryl sulphate; and salts of sulphonated aromatic compounds, for example dodecylbenzene-sulphonate, sodium, calcium and ammonium lignosulphonate, butylnaphthalene sulphonate, and a mixture of the sodium salts of diisopropyl- and triisopropyl-naphthalenesulphonic acid. Suitable agents of the non-ionic type include, for example, the condensation products of ethylene oxide with fatty alcohols such as oleyl alcohol and cetyl alcohol, or with alkyl phenols such as octyl-phenol, nonylphenol, and octylcresol. Other non-ionic agents are the partial esters derived from long chain fatty acids and hexitol anhydrides, for example sorbitol monolaurate; the condensation products of the said partial esters with ethylene oxide and the lecithins.

The compositions which are to be used in the form of aqueous solutions, dispersions or emulsions are generally supplied in the form of a concentrate containing a high proportion of the active ingredient, the concentrate being diluted with water before use. These concentrates are usually required to withstand storage for prolonged periods and after such storage to be capable of dilution with water in order to form aqueous preparations which remain homogeneous for a sufficient time to enable them to be applied by conventional spray equipment.

The compositions of the invention may contain, in addition to carriers and surface-active agents, various other constituents to increase their usefulness. They may contain, for example, buffering salts to maintain the pH of the composition within a desired range; antifreeze agents, for example urea or propylene glycol; adjuvants, for example oils and humectants; and sequestrants, for example citric acid and ethylenediamine-tetracetic acid, which help to prevent the formation of insoluble precipitates when the compositions are diluted with hard water. Aqueous dispersions may contain anti-settling agent and anti-caking agents. The compositions may in general contain a dye or pigment to impart a characteristic colour. Agents for increasing viscosity may be added to reduce the formation of fine droplets during spraying, and thereby reduce spray drift. Other additives useful for particular purposes will be known to those skilled in the formulation art.

In general concentrates may conveniently contain from 10 to 85% and preferably from 25 to 60% by weight of active ingredient. Dilute preparations ready for use may contain varying amounts of the active ingredient, depending upon the purpose for which they are to be used; however, dilute preparations suitable for many uses contain between 0.01% and 10% and preferably between 0.1% and 1% by weight of the active ingredient.

The invention is illustrated by the following Examples, in which all parts are by weight and all temperatures in degrees Centigrade unless otherwise stated.

EXAMPLE 1

This Example illustrates the preparation of Compound nos. 12 to 16 of Table I.

A vigorously stirred solution of 2-nitro-5(2-chloro-4-trifluoromethylphenoxy)N-methanesulphonylbenzamide (40.0 g) in acetone (1250 ml) was treated slowly with titanium trichloride (450 ml, 30% w/v solution in hydrochloric acid) whilst maintaining the temperature below 15°. The reaction mixture was stirred for a further thirty minutes at room temperature, neutralised by the addition of sodium hydroxide solution (to pH 5) and excess sodium bicarbonate solution, and extracted with dichloromethane. The extracts were washed with water, dried and evaporated to give the corresponding 2-amino derivative (30.26 g, m.p. 184°–185°).

A mixture of this material (1.6 g), acetic anhydride (0.4 ml) and acetonitrile (15 ml) was heated under reflux for 2.5 hours, evaporated in vacuo and the residue recrystallised from methanol to give Compound No. 12 (1.5 g, m.p. 201°) of Table I.

Compound Nos. 13, 14 and 15 were prepared similarly using the appropriate anhydride or chloroformate. Compound No. 16 resulted form the reaction of the amine with dimethyl-ammonium N,N-dimethylthiolcarbamate in N,N-dimethyl-formamide.

The 2-nitro-5(2-chloro-4-trifluoromethylphenoxy)N-methanesulphonylbenzamide required as starting material was prepared as follows:

5(2-chloro-4-trifluoromethylphenoxy)-2-nitrobenzoic acid (1.58 g) was heated under reflux in an excess of thionyl chloride (20 ml) for 90 minutes. The excess of thionyl chloride was removed in a vacuum and the remaining oil taken up in dry pyridine (20 ml). Methanesulphonamide (0.45 g) was added and the mixture stirred at room temperature overnight. The pyridine was removed in a vacuum and the remaining oil mixed with 2-molar hydrochloric acid and extracted with ether (2×100 ml). The ether extracts were washed with water (100 ml), dried, and evaporated in a vacuum. The residual solid was recrystallised from isopropanol to give 5-(2-chloro-4-trifluoromethylphenoxy)-2-nitro-N-methanesulphonylbenzamide with a melting point of 201° C. The ether extracts were washed with water (100 ml), dried, and evaporated in a vacuum. The residual solid was recrystallised from isopropanol to give 5-(2-chloro-4-trifluoromethylphenoxy)-2-nitro-N-methanesulphonylbenzamide with a melting point of 201° C.

EXAMPLE 2

This Example illustrates the preparation of Compound No. 17 of Table I.

2-Amino-5(2-chloro-4-trifluoromethylphenoxy)N-methanesulphonylbenzamide (3.0 g, prepared as described in Example 1) was added to a solution of sodium methoxide (from 190 mg of sodium) in methanol (60 ml). The mixture was warmed until dissolution was complete, cooled to 0° and treated with trifluoronitrosomethane until starting material had been consumed. It was then diluted with water, acidified with 2N hydrochloric acid and extracted with ether. The extracts were washed with water and brine, dried and evaporated and the residue recrystallised from toluene/petroleum (b.p. 80°–100°) to give Compound No. 17 (3.3 g) of Table I.

EXAMPLE 3

This Example illustrates the preparation of Compound No. 18 of Table I.

A vigorously stirred solution of 2-nitro-5(2-chloro-4-trifluoromethylphenoxy)N-methanesulphonylbenzamide (4.4 g) in 0.5N sodium hydroxide solution (20 ml) was treated successively with sodium hypophosphite (4.4 g) and 10% palladium on carbon (440 mg). After one hour, the mixture was diluted with water and extracted with ethyl acetate. The extracts were washed with water and brine, dried and evaporated. The residue was triturated with petroleum (b.p. 40°–60°) and recrystallised from acetonitrile to give Compound No. 18 (950 mg) of Table I.

EXAMPLE 4

This Example illustrates the preparation of Compound No. 19 of Table I.

A solution of 2-amino-5(2-chloro-4-trifluoromethylphenoxy)N-methanesulphonylbenzamide (2.03 g) in N sodium hydroxide solution (5 ml) was treated with a solution of sodium nitrite (400 mg) in water (5 ml). The resulting solution was added dropwise to a stirred mixture of conc. hydrochloric acid (7.5 ml) and water (2.5 ml) cooled to 5°. The diazonium chloride was filtered off, washed with ether and heated in water (20 ml), on a steam bath, for thirty minutes. The mixture was cooled and filtered. The solid was dried and recrystallised from toluene to give Compound No. 19 (1.06 g) of Table I.

EXAMPLE 5

This Example illustrates the preparation of Compound No. 20 of Table I.

A mixture of sodium hydride (2.3 g, 50% dispersion in mineral oil, prewashed with petroleum, b.p. 40°–60°) and 4-hydroxy-2-methylbenzoic acid (3.4 g) in dry N,N-dimethylformamide (30 ml) was stirred for thirty minutes, then treated with 3-chloro-4-fluorobenzotrifluoride (4.5 g). The mixture was heated at 130° for five hours, cooled, diluted with water, acidified with 2N hydrochloric acid and extracted with ethyl acetate. The extracts were washed with water and brine, dried and evaporated. The residue was recrystallised from petroleum (b.p. 80°–100°) to give 2-methyl-5(2-chloro-4-trifluoromethylphenoxy)-benzoic acid (2.06 g, m.p. 113°). A suspension of this material (1.34 g) in thionyl chloride (5 ml) was heated under reflux for one hour and the excess reagent removed in vacuo. The residue was dissolved in acetonitrile and again evaporated to give crude acid chloride.

A mixture of methanesulphonamide (0.41 g), potassium carbonate (1.15 g) and methyl ethyl ketone (10 ml) was heated under reflux for thirty minutes, then treated dropwise over a period of two hours with a solution of the acid chloride in methyl ethyl ketone (10 ml). After heating for a further one hour, the mixture was cooled, diluted with water, acidified with 2N hydrochloric acid and extracted with ethyl acetate. The extracts were washed with water and brine, dried and evaporated and the residue recrystallised from toluene/petroleum to give Compound No. 20 (0.56 g) of Table I.

EXAMPLE 6

This Example illustrates the preparation of Compound No. 22 of Table I.

(a) 2,4,5-Trichlorophenol (20 g) in dry dimethylacetamide (40 ml) was treated with sodium hydride (5.28 g of 50% dispersion in oil) in portions and the resulting mixture heated to 120° C. Ethyl-5-chloro-2-nitrobenzoate (16.5 g) was added in solution in dry dimethylacetamide (60 ml) and the mixture heated at 160° C. for ten hours. The solvent was removed and the residue washed with water and extracted with ether. The ether solution was extracted with ether. The ether solution was evaporated. The remaining oil solidified and was recrystallised from ethanol to give ethyl 5(2,4,5-trichlorophenoxy)-2-nitrobenzoate (10.9 g) with a melting point of 99°–102° C.

(b) The product from (a) was heated at 70° C. in isopropanol (50 ml) with a solution of sodium hydroxide (1.02 g) in water (30 ml) for eight hours. The isopropanol was removed and the residue acidified with dilute hydrochloric acid and extracted with methylene dichloride. The methylene dichloride extract yielded an oil which crystallised and was recrystallised from toluene to give 2-nitro-5-(2,4,5-trichlorophenoxy)benzoic acid (5.5 g) with a melting point of 157°–161° C.

(c) The product from (b) (4 g) was heated under reflux in thionyl chloride (20 ml) for four hours. Removal of the excess of thionyl chloride gave an oil (4 g) which solidified on standing.

(d) The acid chloride (2 g) prepared in (c) above in dry methyl ethyl ketone (20 ml) was added dropwise over a period of two hours to a solution of methanesulphonamide (0.75 g) in dry methyl ethyl ketone (10 ml) containing anhydrous potassium carbonate (1.1 g) and maintained at reflux temperature. The mixture was heated for another three hours and then left overnight. The mixture was stirred with dilute hydrochloric acid (100 ml) and extracted with ethyl acetate (150 ml). Evaporation of the ethyl acetate gave an oil which solidified when triturated with dilute hydrochloric acid. The solid was recrystallised from toluene to give Compound No. 22, with a melting point of 170°–171° C.

EXAMPLE 7

This Example illustrates the preparation of Compound No. 23 of Table I.

(a) 2-Nitro-5-(2-chloro-4-trifluoromethyphenoxy)-benzoic acid (10 g) in a mixture of 1,2-dichloroethane (50 ml) and concentrated sulphuric acid (50 ml) was cooled to −5° C. and potassium nitrate (2.79 g) added slowly, keeping the temperature below 0° C. The mixture was stirred for another 1.5 hours, allowed to warm to room temperature and stirred for another hour. The mixture was poured on to ice and the resulting mixture extracted with chloroform. The chloroform extract gave an oil which was shaken with ether and sodium bicarbonate solution. The bicarbonate solution was washed with ether and acidified to give an oil. The oil was extracted with ether. The extract gave a pale yellow oil (8.1 g). This was dissolved in ether/hexane and cooled, when the product crystallised out. The carboxylic acid was converted to the aid chloride by treatment with thionyl chloride, as in Example 6(c).

(b) The product from (a) (3 g) in dry pyridine (15 ml) was cooled to 0° C. and treated with methanesulphonamide. The mixture was left at room temperature for 24 hours and poured on to ice. Acidification gave a brown solid. This was taken up in ether, and the solution filtered and added to hexane with stirring to give a white solid (0.7 g). Recrystallisation from chloroform/hexane gave Compound No. 23 (0.53 g) with a melting point of 206° C. (softened and resolidified at 120° C.).

This compound was also prepared by nitrating 5-(2-chloro-4-trifluoromethylphenoxy)-2-nitro-N-methanesulphonylbenzamide by the method described in paragraph (a) above.

EXAMPLE 8

This Example illustrates the preparation of Compound No. 38 of Table I.

Methyl 5-fluoro-2-nitrobenzoate was reacted with the sodium salt of 4-chloro-3-methylphenol (prepared from sodium hydride and the phenol) in dimethylformamide at 100° C. for 2.5 hours and the resulting methyl 5(4-chloro-3-methylphenoxy)-2-nitrobenzoate isolated in the usual way; the ester had a melting point of 85°–87° C.

The ester was then hydrolysed to the corresponding carboxylic acid. This was converted to the corresponding carboxylic acid chloride and reacted with methanesulphonamide in the presence of pyridine as acid acceptor to give Compound No. 38.

EXAMPLE 9

This Example describes the preparation of Compound 26 of Table I.

Copper chromite (0.15 g) was added to a stirred solution of the tetrafluoroborate salt of Compound 19 (1.43 g) and tetrabutylammonium thiocyanate (1.1 g) in acetonitrile (10 ml). After 1 hour, the mixture was poured into water and extracted with ethyl acetate. The extracts were washed with water, dried and evaporated. The oil so obtained was chromatographed on silica gel in acetonitrile to give an oily product (1.0 g). Trituration with isopropanol gave compound no. 26 (0.42 g) with a melting point of 135° decomp.

EXAMPLE 10

This Example describes the preparation of compound 27 of Table I.

Sodium azide (1.6 g) was added in one portion to a solution of the tetrafluoroborate salt of compound 19 (2.0 g) in acetone (80 ml). After thirty minutes the acetone (80 ml). After thirty minutes the acetone was removed under reduced pressure. The residue was shaken with ethyl acetate and water and the ethyl acetate extracts washed with water and brine, dried, and evaporated. The residue was triturated with ether/petroleum (b.p. 40°–60°). The solid so obtained was recrystallised from carbon tetrachloride to give compound 27 (1.02 g) with a melting point of 119°(decomp.)

EXAMPLE 11

This Example describes the preparation of compound no. 29 of Table I. The tetrafluoroborate salt of compound no. 19 (4.3 g) was added in portions to stirred trimethylphosphite (50 ml) while the temperature was kept at 25°–30° by external cooling. After a further hour, the mixture was diluted with water and extracted with ethyl acetate. The extract was washed with water and then with brine, dried, and evaporated. The residue was triturated with ether to give compound no. 29 (0.8 g) with a melting point of 159°(decomp.).

EXAMPLE 12

This Example illustrates the preparation of N-(methoxycarbonylmethanesulphonyl)-5-(2-chloro-4-trifluoromethylphenoxy)-2-nitrobenzamide (compound no. 7 of Table I).

5-(2-chloro-4-trifluoromethylphenoxy)-2-nitrobenzoic acid (2.36 g) was heated under reflux in thionyl chloride (20 ml) for 90 minutes. The mixture was cooled and the excess of thionyl chloride removed under reduced pressure. Toluene was twice added and removed under reduced pressure. The remaining oil was diluted with butyl acetate (35 ml) and heated under reflux with methoxycarbonylmethanesulphonamide (1 g) and caesium fluoride (3 g) for 20 hours. The mixture was poured into water and extracted with ethyl acetate. The extracts were washed with water, dried, and evaporated to give a oil. This was diluted with ether and the ether solution treated with charcoal and diluted with light petroleum. The yellow solid which separated was purified by thin layer chromatography using silica gel as the solid phase and acetonitrile as the eluent. The chromatography gave an oil which crystallised on addition of ether/light petroleum to give the required compound (0.31 g) with a melting point of 158°–160° C.

EXAMPLE 13

This Example illustrates the preparation of compound no. 6 of Table I. 5-(2-chloro-4-trifluoromethylphenoxy)-2-nitro benzoic acid (3.62 g) was heated under reflux in thionyl chloride (30 ml) for 2 hours. The excess of thionyl chloride was removed and the residue twice evaporated with toluene. The remaining oil was diluted with butyl acetate and heated under reflux with 3-chloropropanesulphonamide (1.58 g) and caesium fluoride (3 g) for 9 hours. The cooled reaction mixture was diluted with water and extrcted with ethyl acetate. The aqueous solution was acidified with dilute hydrochloric acid and extracted with more ethyl acetate. The combined extracts were dried and evaporated to give an oil. This was taken up in carbon tetrachloride and the solution decolourised with charcoal and cooled. Slow addition of petroleum (b.p. 40–60) gave an oily solid. This was taken up in a mixture of chloroform, acetone, and acetic acid (90:10:5) and the solution passed through a column of silica gel. The solution was evaporated and the residue purified by thin layer chromatography on silica gel plates, using a mixture of chloroform, acetone, and acetic acid (90:10:5) as eluent. The principal component was extracted from the silica gel plates with ethanol. The ethanol was evaporated and the residue agitated with dilute hydrochloric acid and ethyl acetate. The ethyl acetate extract was washed with water, dried, and evaporated. The residue was crystallised from a mixture of ether and petroleum (b.p. 30°–40°) and the required compound obtained (0.9 g) as a solid of melting point 116°–119°.

EXAMPLE 14

This Example illustrates the preparation of N-benzenesulphonyl-5-(2-chloro-4-trifluoromethylphenoxy)-2-nitrobenzamide (Compound no. 1 of Table 1).

5-(2-Chloro-4-trifluoromethylphenoxy)-2-nitrobenzoic acid (2 g) was heated under reflux in thionyl chloride (15 ml) for 90 minutes. The excess of thionyl chloride was removed under reduced pressure and the residue diluted with toluene. The toluene was removed under reduced pressure and the remaining oil taken up in butyl acetate. Benzenesulphonamide (1.3 g) and caesium fluoride (4.0 g) were added and the mixture was stirred and heated under reflux for 90 minutes. The mixture was cooled, diluted with water, acidified (HCl) and extracted with ethyl acetate. The extract was washed with water, dried, and evaporated to give an oil. Trituration with carbon tetrachloride and petroleum gave a solid. This was recrystallised from a mixture of carbon tetrachloride, ether, and petroleum to give the required compound (1.11 g), with a melting point of 123°–125°.

EXAMPLE 15

This Example illustrates the preparation of N-methanesulphonyl-5-(2-methanesulphinyl-4-trifluoromethylphenoxy)-2-nitrobenzamide (compound 28 of Table I).

(a) Preparation of methyl 5-(2-methanesulphinyl-4-trifluoromethylphenoxy)-2-nitrobenzoate Methyl 5-(2-amino-4-trifluoromethylphenoxy)-2-nitrobenzoate (8 g) in concentrated hydrochloric acid (35 ml) was cooled to 0°–5° and stirred vigorously while a solution of sodium nitrite (1.86 g) was added dropwise, keeping the temperature at 0°–5°. The mixture was stirred for 30 minutes and then filtered into a solution of sodium fluoborate (5.44 g) in water (6 ml). The precipitated diazonium fluoborate salt (8.74 g) was washed with aqueous sodium fluoborate, cold ethanol, and ether.

The diazonium salt so prepared (8.74 g) in dry dimethylsulphoxide (20 ml) was added dropwise to a stirred solution of potassium iodide (6.38 g) in dry dimethyl sulphoxide (30 ml) and the mixture stirred for 1 hour at room temperature. The mixture was then poured into water and extracted with ehter. The ether extract was washed with water, dried, treated with charcoal, and evaporated to give an oil. This was extracted several times with petroleum (b.p. 60°–80°). The petroleum extracts yielded methyl 5-(2-iodo-4-trifluoromethylphenoxy)-2-nitro benzoate upon evaporation. The residue from the extraction was taken up in ether and applied to preparative chromatographic plates coated with silica gel. The plates were eluted with chloroform containing 2% of ethanol. Two products were separated; the first was the iodo compound (6 g) referred to above. The second product (0.95 g) was identified as the required methanesulphinyl compound.

(b) Preparation of compound 28

The methanesulphinyl compound (0.95 g) from (a) was hydrolysed to 5-(2-methanesulphinyl-4-trifluoromethylphenoxy)-2-nitro benzoic acid by treatment with a mixture of acetic acid and aqueous hydrobromic acid as described in paragraph (c) of Example 16. The substituted benzoic acid so obtained was converted to its acid chloride and treated with methanesulphonamide and caesium fluoride in refluxing butyl acetate as described in paragraph (d) of Example 16 to give compound 28 with a melting point of 158°–160°.

EXAMPLE 16

This Example illustrates the preparation of N-methanesulphonyl-5-(2,3,5,6-tetrafluoro-4-trifluoromethylphenoxy)-2-nitrobenzamide (compound 30 of Table I).

(a) Preparation of ethyl 5-(2,3,5,6-tetrafluoro-4-trifluoromethylphenoxy)benzoate Pentafluorobenzotrifluoride (11.8 g) was stirred in dry dimethylsulphoxide (75 ml) with ethyl 3-hydroxy benzoate (8.3 g) and anhydrous potassium carbonate (7.0 g) for 2 hours and then kept overnight. The mixture was poured into water (600 ml) and extracted with ether (2×250 ml). The extract was washed with water (400 ml), dried, and evaporated to give a colourless liquid (18.4 g) identified as the required ester.

(b) Preparation of ethyl 5-(2,3,5,6-tetrafluoro-4-trifluoromethylphenoxy)-2-nitro benzoate.

The ester from (b) (15.28 g) in 1,2-dichloroethane (100 ml) was cooled to 0° C. and stirred while concentrated sulphuric acid (100 ml) was added in portions, keeping the temperature below 5°. The mixture was then cooled to 0° and potassium nitrate (4.44 g) added in portions over a period of 75 minutes, keeping the temperature below 5° C. The mixture was then stirred for another hour at 5° and poured on to ice (500 ml). The mixture was extracted with ether (3×200 ml). The ether extract was washed with water (5×500 ml) until the washings were neutral. The extract was dried (MgSO$_4$) and evaporated to give an oil which solidified on cooling. This was washed with petroleum (b.p. 30°–40°) to give a colourless solid (13.4 g) identified as the required nitro compound. A sample recrystallised from petroleum (b.p. 60°–80°) had a melting point of 77°–78°.

(c) Preparation of 2-nitro-5-(2,3,5,6-tetrafluoro-4-trifluoromethylphenoxy)benzoic acid The product from (b) (9.0 g) was stirred and heated under reflux with a mixture of acetic acid (180 ml) and 40% aqueous hydrobromic acid (90 ml) for 6.25 hours. The mixture was cooled, left overnight, and evaporated under reduced pressure. Toluene was twice added to the residue and evaporated off under reduced pressure. The remaining solid was recrystallised from a mixture of toluene (80 ml) and petroleum (b.p. 80°–100°, 120 ml), giving the required acid (6.5 g) with a melting point of 138.5°–139.5°.

(d) Preparation of compound 30

The product from (c) (3.5 g) was heated under reflux in thionyl chloride (60 ml) for 3 hours. The excess of thionyl chloride was removed under reduced pressure and the residue heated and stirred under reflux with dry caesium fluoride (3.3 g) and methanesulphonamide (1.67 g) in dry butyl acetate (50 ml) for 2.5 hours. The solution was cooled, and diluted with ethyl acetate, (150 ml) and dilute hydrochloric acid. The organic layer was separated, washed with water (3×200 ml) and dried. Removal of the solvent under reduced pressure gave a colourless solid (3.5 g), which was washed with petroleum (b.p. 30°–40°) and recrystallised from isopropanol to give compound no. 30 with a melting point of 177°–177.5°.

EXAMPLE 17

This Example illustrates the preparation of N-methanesulphonyl 5-(2-chloro-5-trifluoromethylphenoxy)-2-nitro benzamide (compound 32 of Table I) and N-methane-sulphonyl-3-(2-chloro-5-trifluoromethylphenoxy)benzamide (compound 31).

(a) Preparation of 4-chloro-3-fluorobenzotrifluoride

3-Amino-4-chlorobenzotrifluoride was diazotised by the standard procedure and the diazonium salt isolated as the fluoborate. This material was heated to decomposition with a Bunsen burner flame. The 4-chloro-3-fluorobenzotrifluoride distilled off and was redistilled at atmospheric pressure (b.p. 128°).

(b) Preparation of 3(2-chloro-5-trifluoromethylphenoxy) benzoic acid

3-Hydroxybenzoic acid (3.45 g) was added to a solution of potassium hydroxide (2.8 g) in methanol. The solution was evaporated under reduced pressure to give a white solid. This was taken up in dry dimethylsulphoxide (25 ml). The resulting solution was stirred and heated at 170° with anhydrous potassium carbonate (1.25 g) and 4-chloro-3-fluorobenzotrifluoride (5 g) for 12 hours. The mixture was then cooled and poured into water, (500 ml). The mixture was extracted with ether and then acidified (HCl). The precipitate which formed was recrystallised from petroleum (b.p. 60°–80°) to give the required acid (4.5 g) with a melting point of 142°–143°.

(c) Preparation of 5-(2-chloro-5-trifluoromethylphenoxy)-2-nitrobenzoic acid The acid from (b) (2.0 g) was added to a mixture of concentrated sulphuric acid (15 ml) and 1,2-dichloroethane (10 ml) kept at 0°. Potassium nitrate (1.2 g) was then added in portions with stirring over a period of 30 minutes, keeping the temperature at 0°. The mixture was stirred for a further hour at 0° and then for 3 hours at room temperature. The mixture was then poured on to ice and extracted with ethyl acetate. The extract was washed with water, dried, and evaporated to give a dark gum. This was extracted several times with boiling cyclohexane. The residue crystallised on cooling and was identified as the required nitro-acid, with a melting point of 147°–148°.

(d) Preparation of compound 32

The nitro-acid from (c) (0.8 g) was heated under reflux with thionyl chloride (25 ml) for 3 hours. The excess of thionyl chloride was removed under reduced pressure and the remaining oil taken up in pyridine (20 ml). Methanesulphonamide (0.5 g) was added and the mixture stirred and heated under reflux for 3 hours. The pyridine was removed under reduced pressure and the residue agitated with ethyl acetate and dilute hydrochloric acid. The ethyl acetate layer was washed with water, dried, and evaporated to give a brown gum. Trituration with cold ether gave a beige solid identified as compound 32, having a melting point of 204°–205°.

(e) Preparation of compound 31

The acid from (b) (0.8 g) was treated with thionyl chloride followed by methanesulphonamide and pyridine as described in paragraph (d) above for compound 32. The product was recrystallised from a mixture of ether and petroleum (b.p. 40°–60°) to give compound 31 with a melting point of 132°–133°.

EXAMPLE 18

This Example illustrates the preparation of N-methanesulphonyl-5-(2-chloro-4-trifluoromethylphenoxy)-2-trifluoromethylbenzamide (Compound 37 of Table I).

Finely powdered methyl 2-amino-5(2-chloro-4-trifluoromethylphenoxy)benzoate (16.5 g) was suspended in fluoboric acid (120 ml, 40%), treated with ethanol (100 ml) and cooled to 0°. A solution of sodium nitrite (4.5 g) in water (20 ml) was added dropwise to the stirred reaction mixture. After a further fifteen minutes at 0°, the crystalline precipitate was filtered off and washed with ether to give the diazonium fluoborate (12.32 g).

Sodium iodide (4.5 g) was added to a stirred solution of the diazonium salt (11.7 g) in acetonitrile (100 ml). After stirring at 20° for fifteen minutes, effervescence had ceased. The solvent was removed in vacue and the residue partitioned between dichloromethane and water. The extracts were washed with water, dried and evaporated. The crude product was flash chromatographed on silica in ether to give 10.2 g of a mixture of methyl 2-iodo-5(2-chloro-4-trifluoromethylphenoxy)-benzoate and its 2-H derivative (80:20 by GLC).

This material (2.0 g) was heated in a sealed Teflon lined pressure vessel for eighteen hours at 150° together with trifluoromethyl iodide (5 ml), acetonitrile (15 ml), dry pyridine (5 ml) and dry, freshly precipitated, copper powder (2.5 g). The crude reaction mixture was filtered through Supercel, evaporated in vacuo, dissolved in ether, washed with 2N hydrochloric acid and water, dried and chromatographed on silica in ethyl acetate/petroleum, b.p. 60°–80° (1:3). Pure methyl 2-trifluoromethyl-5(2-chloro-4-trifluoromethylphenoxy)-benzoate (600 mg.), was obtained together with material contaminated with 2H-derivative. Rechromatography of the latter gave an additional 250 mg of pure material.

The 2-CF$_3$ ester (1.62 g) was treated with potassium hydroxide (230 mg), water (3 ml) and methanol (40 ml) and stirred at 60° for six hours. The mixture was cooled, diluted with water, extracted with ether to remove unchanged ester, acidified with 2N hydrochloric acid and extracted with ethyl acetate. The latter extracts were washed with water and brine, dried and evaporated and the residue chromatographed on silica gel in dichloromethane to give an oil which crystallized slowly on standing to a white solid 1.08 g, m.p. 81° identified as 5-(2-chloro-4-trifluoromethylphenoxy)-2-trifluoromethylbenzoic acid.

This material (0.69 g) was converted into its acid chloride and then by treatment of the latter with methanesulphonamide in methyl ethyl ketone in the presence of anhydrous potassium carbonate into compound 37, following the procedures described in paragraphs (c) and (d) of Example 6.

EXAMPLE 19

This Example illustrates the herbicidal properties of compounds of Table I. The compounds were submitted to herbicide tests as described below.

Each compound was formulated for test by mixing an appropriate amount of it with 5 ml of an emulsion prepared by diluting 160 ml of a solution containing 21.1 grams per liter of Span 80 and 78.2 grams per liter of Tween 20 in methylcyclohexanone to 500 ml with water. Span 80 is a Trade Mark for a surface-active agent comprising sorbitan monolaurate. Tween 20 is a Trade Mark for a surface-active agent comprising a condensate of 20 molar proportions of ethylene oxide with sorbitan monolaurate. The mixture of the compound and the emulsion was then shaken with glass beads and diluted to 40 ml with water. The spray composition so prepared was sprayed on to young pot plants (post-emergence test) of the species named in Table IV below, at a rate equivalent to 1000 liters per hectare. Damage to plants was assessed 14 days after spraying by comparison with untreated plants, on a scale of 0 to 5 where 0 is 0 to 20% damage and 5 is complete kill. In the table of results, a dash (-) means that no test was made.

A test was also carried out to detect pre-emergence herbicidal activity. Seeds of the test species were placed on the surface of fibre trays of soil and were sprayed with the compositions at the rate of 1000 liters per hectare. The seeds were then covered with further soil. Three weeks after spraying, the seedlings in the sprayed fibre trays were compared with the seedlings in unsprayed control trays, the damage being assessed on the same scale of 0 to 5.

The results of the tests are given in Table IV below.

TABLE IV

| COMPOUND NO | RATE OF APPLICATION kg/ha | PRE- OR POST-EMERGENCE APPLICATION | TEST PLANTS | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|
| | | | Sb | Rp | Ct | Sy | Mz | Ww | Rc | Sn | Ip | Am | Pi | Ca | Po | Xs | Xa | Ab | Cv | Ot/Av | Dg | Pu | St | Ec | Sh | Ag | Cn | | | | | |
| 1 | 5.0 | Pre | 5 | 5 | 1 | 0 | 2 | 0 | 1 | 5 | 4 | 5 | — | — | 5 | 5 | — | 5 | — | 0 | 1 | 1 | 4 | — | 5 | 5 | 0 | 0 | 0 | 4 | 0 |
| | | Post | 5 | 5 | 4 | 2 | 4 | 3 | 2 | 5 | — | 5 | — | 4 | 5 | 5 | — | 5 | 5 | 3 | 4 | 4 | 5 | 5 | 5 | 2 | 1 | 4 |
| 2 | 5.0 | Pre | 5 | 5 | 0 | 0 | 0 | 0 | 0 | 4 | 5 | 5 | — | 5 | 5 | 4 | 0 | 5 | 4 | 0 | 2 | 0 | 4 | 4 | 2 | 2 | 0 | 2 |
| | | Post | 4 | 4 | 4 | 1 | 5 | 0 | 0 | 4 | 2 | 5 | — | 4 | 5 | 4 | 0 | 4 | 3 | 0 | 4 | 0 | 4 | 5 | 5 | 0 | 0 | 1 |
| 3 | 5.0 | Pre | 4 | 4 | 0 | 1 | 0 | 0 | 0 | 4 | 2 | 5 | — | 5 | 5 | 3 | 0 | 4 | 3 | 0 | 2 | 0 | 3 | 4 | 4 | 0 | 0 | 0 |
| | | Post | 4 | 4 | 4 | 1 | 4 | 0 | 0 | 5 | 2 | 5 | 0 | 4 | 5 | 4 | 0 | 4 | — | 0 | 4 | 0 | 4 | 5 | 5 | 0 | 0 | 0 |
| 4 | 5.0 | Pre | 2 | 2 | 2 | 2 | 2 | 0 | 1 | 2 | 0 | 5 | 2 | 2 | 4 | 3 | 0 | 2 | 1 | 0 | 2 | 0 | 3 | 3 | 3 | 0 | 1 | 0 |
| | | Post | 2 | 2 | 1 | 2 | 0 | 0 | 0 | 4 | 2 | 5 | 4 | 4 | 5 | 2 | 0 | 4 | — | 1 | 3 | 0 | 2 | 2 | 2 | 0 | — | 0 |
| 5 | 1.0 | Pre | 0 | 0 | 0 | 0 | 2 | 0 | 0 | 0 | 2 | 5 | 4 | 2 | 5 | 2 | 0 | 0 | — | 0 | 0 | 0 | 0 | — | — | — | 0 | 0 |
| | | Post | 5 | 5 | 4 | 0 | 4 | 0 | 0 | 5 | 4 | 5 | 5 | 4 | 5 | 4 | 0 | 4 | — | 1 | 4 | 0 | 4 | 4 | 5 | 1 | 0 | 3 |
| 6 | 5.0 | Pre | 4 | 4 | 4 | 0 | 2 | 4 | 2 | 4 | 4 | 5 | 5 | 4 | 5 | 5 | 0 | 5 | — | 2 | 4 | 4 | 4 | 4 | 4 | 2 | 3 | 0 |
| | | Post | 5 | 5 | 5 | 3 | 4 | 4 | 3 | 5 | 5 | 5 | 5 | 4 | 5 | 5 | 0 | 5 | — | 2 | 4 | 4 | 4 | 5 | 5 | — | 4 | 3 |
| 7 | 5.0 | Pre | 5 | 5 | 5 | 4 | 4 | 4 | 3 | 5 | 5 | 5 | 5 | 5 | 5 | 5 | 3 | 4 | — | 2 | 4 | 4 | 5 | 4 | 5 | 4 | — | — |
| | | Post | 3 | 3 | 4 | 0 | 2 | 3 | 2 | 5 | 3 | 5 | 4 | 4 | 5 | 3 | 5 | 5 | — | 2 | 5 | 0 | 5 | 4 | 4 | — | — | 2 |
| 8 | 1.0 | Pre | 4 | — | 4 | 1 | 0 | 2 | 1 | 0 | — | 2 | — | 4 | 5 | — | 0 | 4 | — | 2 | 4 | 2 | 4 | 2 | — | — | — | 2 |
| | | Post | — | 0 | 0 | 0 | 0 | 0 | 0 | 0 | 0 | 0 | 4 | 0 | — | 0 | 0 | 0 | 3 | 0 | 0 | — | 2 | 0 | — | 0 | 0 | — |
| 12 | 5.0 | Post | 0 | 0 | 0 | 0 | 1 | 0 | 0 | 0 | 0 | — | 0 | 0 | 0 | — | 0 | 2 | 3 | 0 | 0 | 0 | 0 | 2 | 0 | 0 | 0 | 0 |
| 13 | 5.0 | Post | 0 | 1 | 0 | 0 | 0 | 0 | 0 | 0 | 0 | — | 2 | 2 | 2 | — | 0 | 0 | 3 | 0 | 0 | 0 | 0 | 2 | 0 | 0 | 0 | 0 |
| 14 | 5.0 | Post | 1 | 2 | 1 | 0 | 1 | 0 | 0 | 0 | 0 | — | 1 | 2 | 0 | — | 0 | 2 | 2 | 0 | 0 | 0 | 0 | 2 | 0 | 0 | 0 | 0 |
| 17 | 5.0 | Post | 2 | 2 | 0 | 0 | — | 0 | 0 | 0 | 0 | — | 0 | — | 4 | — | 0 | 0 | 0 | 0 | 0 | 0 | 0 | 2 | 0 | 0 | 0 | 0 |
| 18 | 4.0 | Post | — | — | 0 | 0 | — | 0 | 0 | 0 | — | 4 | — | — | — | — | — | 0 | 3 | — | — | 0 | 0 | — | — | 0 | 2 | 0 |
| 21 | 2.5 | Post | 1 | 1 | 0 | 0 | 1 | 0 | 0 | 0 | 0 | 5 | — | 2 | — | — | — | 0 | 3 | 0 | 0 | 0 | 0 | 3 | 0 | 2 | 0 | — |
| 22 | 3.0 | Post | 2 | 3 | 0 | 0 | 1 | 1 | 0 | 2 | 1 | 5 | 2 | 4 | 4 | — | 2 | 0 | 2 | 0 | 1 | 0 | 3 | 4 | 4 | 1 | 0 | 3 |
| 24 | 5.0 | Pre | 1 | 2 | 0 | 0 | 1 | 0 | 0 | 2 | 0 | 5 | — | — | — | — | 2 | 0 | 0 | — | 0 | 0 | 2 | — | — | 0 | 2 | 0 |
| | | Post | 2 | 2 | 1 | 0 | 0 | 2 | 0 | 0 | 0 | 5 | 0 | 4 | 0 | — | 2 | 0 | 2 | — | 0 | 0 | 0 | 4 | 0 | — | 0 | — |
| 25 | 3 | Post | 4 | 4 | 0 | 0 | 0 | 0 | 0 | 5 | 0 | 5 | 0 | 4 | 4 | — | 4 | 2 | 2 | — | 0 | 0 | 2 | 4 | 0 | 0 | 0 | 0 |
| 26 | 5 | Pre | 1 | 2 | 0 | 0 | 0 | 0 | 0 | 0 | 0 | — | 0 | — | — | — | — | 0 | 0 | — | 0 | 0 | 0 | 0 | 0 | 0 | 0 | 0 |
| | | Post | 4 | 4 | 4 | 3 | 4 | 3 | 3 | 2 | 3 | 5 | — | 4 | 5 | — | 2 | 2 | 2 | — | 1 | 1 | 3 | 3 | 3 | 0 | 2 | 2 |
| 27 | 5 | Pre | 1 | 2 | 1 | 0 | 0 | 0 | 0 | 2 | 0 | — | — | — | 0 | — | — | 0 | — | — | 0 | 0 | 0 | 0 | 0 | 0 | 0 | 0 |
| | | Post | 3 | 3 | 2 | 0 | 2 | 0 | 0 | 2 | 2 | 5 | 2 | 4 | 5 | — | 4 | 0 | 0 | — | 1 | 0 | 3 | 0 | 5 | 1 | 0 | 2 |
| 28 | 1 | Post | 2 | 2 | 2 | 2 | 0 | 0 | 2 | 4 | 0 | 5 | 4 | 4 | 5 | — | 2 | 2 | — | — | 0 | 0 | 3 | 4 | 3 | 0 | 0 | 0 |
| 30 | 1 | Post | 0 | 0 | 2 | 1 | 0 | 0 | 1 | 5 | 5 | 5 | — | 4 | 5 | — | 4 | 2 | — | — | 1 | 0 | 5 | 5 | 4 | 0 | 0 | 0 |
| 31 | 5.0 | Pre | 1 | 0 | 1 | 0 | 0 | 0 | 0 | 0 | 0 | — | — | 0 | 0 | — | — | 0 | 0 | — | — | 0 | 0 | 5 | 0 | 0 | 0 | 0 |
| | | Post | 1 | 1 | 0 | 0 | 0 | 0 | 0 | 0 | 0 | 5 | — | 4 | 0 | — | — | 0 | 3 | — | 4 | 0 | 4 | 0 | 4 | 0 | 0 | — |
| 32 | 2.0 | Post | 0 | 0 | 1 | 0 | 0 | 0 | 0 | 0 | 2 | 5 | — | — | 2 | — | — | 0 | 0 | — | 0 | 0 | 0 | 0 | 4 | 0 | 0 | 2 |
| 33 | 5.0 | Pre | 2 | 2 | 1 | 0 | 0 | 2 | 2 | 2 | 0 | 5 | — | 1 | 4 | — | — | 0 | — | — | 0 | 0 | 0 | 2 | 0 | 0 | 0 | 0 |
| | | Post | 2 | 2 | 0 | 1 | 4 | 3 | 2 | 2 | 0 | 5 | — | 4 | 5 | — | — | 3 | 0 | — | 0 | 2 | 4 | 2 | 4 | 1 | 0 | 0 |
| 34 | 5.0 | Pre | 5 | 5 | 3 | 1 | 4 | 3 | 2 | 5 | 4 | 5 | — | 4 | 5 | — | 4 | 4 | 4 | — | 2 | 2 | 4 | 4 | 4 | 0 | 0 | 0 |
| 35 | 5.0 | Post | 4 | 5 | 0 | 0 | 4 | 2 | 3 | 5 | 2 | 5 | — | 5 | 5 | — | 0 | 4 | 0 | — | 2 | 0 | 3 | 5 | 5 | 1 | 1 | 0 |
| 36 | 1.0 | Pre | 4 | 4 | 0 | 0 | 0 | 0 | 0 | 0 | — | 5 | 3 | 4 | 4 | — | 0 | 0 | 4 | — | 2 | 0 | 5 | 0 | 0 | 0 | 0 | — |

TABLE IV-continued

| COMPOUND NO | RATE OF APPLICATION kg/ha | PRE- OR POST-EMERGENCE APPLICATION | TEST PLANTS | | | | | | | | | | | | | | | | | | | | | | | |
|---|---|---|---|---|---|---|---|---|---|---|---|---|---|---|---|---|---|---|---|---|---|---|---|---|---|---|
| | | | Sb | Rp | Ct | Sy | Mz | Ww | Rc | Sn | Ip | Am | Pi | Ca | Po | Xs | Xa | Ab | Cv | Ot/Av | Dg | Pu | St | Ec | Sh | Ag | Cn |
| 37 | 0.2 | Post | 0 | 3 | 0 | 0 | 0 | 0 | 0 | 0 | 2 | 0 | 5 | 0 | 3 | 1 | 0 | 2 | 4 | 0 | 0 | 0 | 0 | 0 | 0 | 0 | 0 |
| 37 | 0.2 | Pre | 5 | — | 2 | 0 | 2 | 0 | 0 | 5 | 2 | 5 | 5 | 4 | — | — | 0 | 3 | — | 0 | 3 | — | 4 | — | 3 | 0 | — |
| 37 | 1.0 | Post | 4 | 5 | 2 | 4 | 5 | 3 | 0 | 5 | 5 | 5 | 5 | 4 | — | — | 4 | 3 | — | 2 | 4 | — | 5 | 3 | 5 | 0 | — |
| 37 | 1.0 | Pre | 5 | 5 | 5 | 4 | 4 | 4 | — | 5 | 3 | 5 | 5 | 5 | — | — | 3 | 5 | — | 2 | 4 | — | 4 | 4 | 3 | 2 | 1 |
| 37 | 2.0 | Post | 5 | 5 | 4 | 4 | 4 | 3 | 1 | 5 | 5 | 5 | 5 | 5 | — | — | 4 | 4 | — | 1 | 5 | — | 5 | 4 | 4 | 2 | 2 |
| 38 | 2.0 | Post | 1 | 0 | 1 | 3 | 3 | 0 | 0 | 0 | 2 | 4 | 1 | 2 | 3 | — | 0 | 4 | 3 | 0 | 3 | 0 | 3 | 3 | 0 | 0 | — |

Table V gives herbicide test results for 5-(2-chloro-4-trifluoromethylphenoxy)-2-trifluoromethyl benzoic acid, useful as an intermediate for compound 37 of Table I. The test procedures were the same as for Table IV. This compound is referred to in Table V as compound A. Other intermediates are referred to in Table V under the following code numbers:

| Intermediate 67 | Compound B |
| Intermediate 69 | Compound C |
| Intermediate 70 | Compound D |
| Intermediate 71 | Compound E |

TABLE V

| COMPOUND NO | RATE OF APPLICATION kg/ha | PRE- OR POST-EMERGENCE APPLICATION | TEST PLANTS | | | | | | | | | | | |
|---|---|---|---|---|---|---|---|---|---|---|---|---|---|---|
| | | | Sb | Rp | Ct | Sy | Mz | Ww | Rc | Sn | Ip | Am | Pi | Ca |
| A | 1.0 | Pre | 5 | 4 | 0 | 4 | 1 | 0 | 0 | 4 | 3 | 5 | 5 | 5 |
| | | Post | 3 | 5 | 3 | 3 | 4 | 2 | 0 | 5 | 4 | 5 | 3 | 5 |
| A | 4.0 | Pre | 5 | 5 | — | 3 | 1 | 3 | 2 | 5 | 3 | 5 | 5 | 5 |
| | | Post | 4 | 5 | 4 | 4 | 5 | 3 | 1 | 5 | 4 | 5 | 4 | 4 |
| B | 5.0 | Pre | 4 | 1 | 4 | 1 | 0 | 0 | 0 | 3 | 3 | 5 | 5 | 1 |
| | | Post | 4 | 4 | 3 | 3 | 4 | 1 | 1 | 5 | 4 | — | 4 | 5 |
| C | 5.0 | Pre | 2 | 2 | 1 | 0 | 1 | 1 | 0 | 2 | 3 | 3 | 2 | 3 |
| | | Post | 3 | 3 | 2 | 3 | 3 | 0 | 0 | 5 | 3 | — | 3 | 4 |
| D | 5.0 | Pre | 1 | 0 | 0 | 0 | 0 | 0 | 0 | 3 | 1 | 3 | — | 0 |
| | | Post | 2 | 2 | 2 | 3 | 1 | 0 | 0 | 5 | 4 | 4 | — | 4 |
| E | 5.0 | Pre | 0 | 1 | 0 | 0 | 0 | 0 | 0 | 0 | 0 | 0 | — | 0 |
| | | Post | 1 | 3 | 1 | 4 | 3 | 1 | 0 | 2 | 2 | 3 | — | 3 |

| COMPOUND NO | RATE OF APPLICATION kg/ha | PRE- OR POST-EMERGENCE APPLICATION | TEST PLANTS | | | | | | | | | | | |
|---|---|---|---|---|---|---|---|---|---|---|---|---|---|---|
| | | | Po | Xa | Ab | Cv | Ot/Av | Dg | Pu | St | Ec | Sh | Ag | Cn |
| A | 1.0 | Pre | — | 0 | 4 | — | 0 | 4 | — | 4 | 2 | 1 | 1 | — |
| | | Post | — | 4 | 3 | — | 2 | 3 | — | 5 | 4 | 5 | 0 | 2 |
| A | 4.0 | Pre | — | 1 | 5 | — | 2 | 4 | — | 4 | 4 | 4 | 3 | — |
| | | Post | — | 4 | 5 | — | 4 | 5 | — | 5 | 4 | 5 | 3 | 2 |
| B | 5.0 | Pre | — | 2 | 1 | — | 0 | 2 | — | 3 | 0 | 4 | 0 | — |
| | | Post | — | 4 | 4 | — | 2 | 5 | — | 4 | 3 | 4 | 1 | — |
| C | 5.0 | Pre | — | 0 | 2 | — | 0 | 2 | — | 3 | 3 | 2 | 0 | — |
| | | Post | — | 1 | 3 | — | 2 | 2 | — | 4 | 2 | 2 | 0 | — |
| D | 5.0 | Pre | — | 0 | 0 | — | 0 | 0 | — | 0 | 0 | 0 | 0 | — |
| | | Post | — | 3 | 4 | — | 0 | 2 | — | 3 | 0 | 1 | 0 | — |
| E | 5.0 | Pre | — | 0 | 1 | — | 0 | 0 | — | 0 | 0 | 0 | 0 | — |
| | | Post | — | 1 | 2 | — | 0 | 2 | — | 3 | 1 | 2 | 0 | — |

Names of test plants in Table IV and V

Sb: Sugar beet
Rp: Rape
Ct: Cotton
Sy: Soya bean
Mz: Maize
Ww: Winter wheat
Rc: Rice
Sn: *Senecio vulgaris*
Ip: *Ipomoea purpurea*
Am: *Amaranthus retroflexus*
Pi: *Polygonum aviculare*
Ca: *Chenopodium album*
Po: *Portulaca oleracea*
Xs: *Xanthium spinosum*
Ab: *Abutilon theophrastii*
Cv: *Convolvulus arvensis*
Ot/Av: Oats (cultivated in pre-emergence test and *Avena fatua* (wild oats) in post-emergence test)
Dg: *Digitaria sanguinalis*
Pu: *Poa annua*
St: *Setaria viridis*
Ec: *Echinochloa crus-galli*
Sh: *Sorghum halepense*
Ag: *Agropyron repens*
Cn: *Cyperus rotundus*

Subject to the foregoing disclaimer regarding the contents of European patent application 79300098.5, what we claim is:

1. A compound of the formula (II)

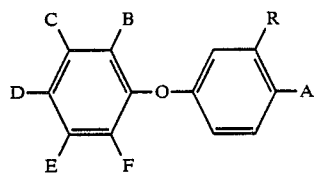

wherein:
A is hydrogen, halogen, alkyl of 1 to 6 carbons, $NO_2$ or $CF_3$;
B is hydrogen, halogen, alkyl of 1 to 6 carbons, $CF_3$ or $NO_2$;
C is $CF_3$, hydrogen or halogen;
D is halogen or $CF_3$;
E is hydrogen or halogen;
F is hydrogen, halogen or $CF_3$; and
R is a group —$CONHSO_2R^3$ wherein $R^3$ is substituted alkyl of 1 to 4 carbons wherein the substitution is alkoxy of 1 to 4 carbons.

2. A compound as claimed in claim 1 wherein A is $NO_2$, B is Cl, C, E and F are each hydrogen, D is $CF_3$ and R is —$CONHSO_2CH_2CH_2OCH_3$.

3. A compound as claimed in claim 1 wherein
the group A is $NO_2$, methyl or trifluoromethyl;
B is fluorine or chlorine;
C is hydrogen;
D is fluorine, chlorine, bromine, iodine, or $CF_3$;
E is hydrogen;
F is hydrogen, fluorine, chlorine, bromine, iodine, or $CF_3$;

and R is a —CONHSO$_2$R$^3$ group wherein R$^3$ is substituted alkyl group of 1 to 4 carbon atoms wherein the substitution is alkoxy of 1 to 4 carbon atoms.

4. A method of inhibiting the growth of unwanted plants which comprises applying to the said plants a herbicidally effective amount of a compound according to claim 1.

5. The method of claim 4, wherein the unwanted plants are selectively inhibited in the presence of wheat.

* * * * *